US012773409B2

(12) United States Patent
Mar

(10) Patent No.: US 12,773,409 B2
(45) Date of Patent: Oct. 27, 2026

(54) TREATMENT OF EOSINOPHILIC DISORDERS WITH AVAPRITINIB

(71) Applicant: Blueprint Medicines Corporation, Cambridge, MA (US)

(72) Inventor: Brenton Mar, Cambridge, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 830 days.

(21) Appl. No.: 17/766,200

(22) PCT Filed: Oct. 5, 2020

(86) PCT No.: PCT/US2020/054221
§ 371 (c)(1),
(2) Date: Apr. 1, 2022

(87) PCT Pub. No.: WO2021/067917
PCT Pub. Date: Apr. 8, 2021

(65) Prior Publication Data

US 2024/0075041 A1 Mar. 7, 2024

Related U.S. Application Data

(60) Provisional application No. 62/910,931, filed on Oct. 4, 2019.

(51) Int. Cl.
*A61K 31/53* (2006.01)
*A61P 35/00* (2006.01)

(52) U.S. Cl.
CPC .............. *A61K 31/53* (2013.01); *A61P 35/00* (2018.01)

(58) Field of Classification Search
CPC ................................ A61K 31/53; A61P 35/00
See application file for complete search history.

(56) References Cited

U.S. PATENT DOCUMENTS

| | | | | |
|---|---|---|---|---|
| 6,982,265 | B1 | 1/2006 | Hunt et al. | |
| 7,244,733 | B2 | 7/2007 | Hunt et al. | |
| 7,329,495 | B2 | 2/2008 | Chen et al. | |
| 8,609,672 | B2 | 12/2013 | Russu et al. | |
| 8,680,124 | B2 * | 3/2014 | Wilhelm | A61P 35/02 514/350 |
| 8,802,697 | B2 | 8/2014 | Bifulco, Jr. et al. | |
| 9,126,951 | B2 | 9/2015 | Bifulco, Jr. et al. | |
| 9,200,002 | B2 | 12/2015 | Hodous et al. | |
| 9,334,263 | B2 | 5/2016 | Hodous et al. | |
| 9,340,514 | B2 | 5/2016 | Bifulco, Jr. et al. | |
| 9,434,700 | B2 | 9/2016 | Bifulco, Jr. et al. | |
| 9,499,522 | B2 | 11/2016 | DiPietro et al. | |
| 9,688,680 | B2 | 6/2017 | Hodous | |
| 9,695,165 | B2 | 7/2017 | Bifulco, Jr. et al. | |
| 9,884,861 | B2 | 2/2018 | Hodous et al. | |
| 9,944,651 | B2 | 4/2018 | Hodous et al. | |
| 9,994,552 | B2 | 6/2018 | DiPietro et al. | |
| 9,994,575 | B2 | 6/2018 | Hodous et al. | |
| 10,000,490 | B2 | 6/2018 | Bifulco, Jr. et al. | |
| 10,000,496 | B2 | 6/2018 | Hodous et al. | |
| 10,017,512 | B2 | 7/2018 | Wenglowsky et al. | |
| 10,030,005 | B2 | 7/2018 | Brubaker et al. | |
| 10,035,789 | B2 | 7/2018 | Brubaker et al. | |
| 10,202,365 | B2 | 2/2019 | Brooijmans et al. | |
| 10,227,329 | B2 | 3/2019 | Brubaker et al. | |
| 10,584,114 | B2 | 3/2020 | Brubaker et al. | |

(Continued)

FOREIGN PATENT DOCUMENTS

| | | |
|---|---|---|
| CN | 101007814 A | 8/2007 |
| CN | 102040494 A | 5/2011 |

(Continued)

OTHER PUBLICATIONS

Evans, E.,A precision therapy against cancers driven by KIT/PDGFRA mutations Science Translational Medicine, V9 pp. 1-11 (Year: 2017).*

Lübke, J., et al. Inhibitory effects of midostaurin and avapritinib on myeloid progenitors derived from patients with KIT D816V positive advanced systemic mastocytosis. Leukemia 33, 1195-1205 (Year: 2019).*

Maric, et al., KIT D816V-associated systemic mastocytosis with eosinophilia and FIP1 L 1/PDGFRA associated chronic eosinophilic leukemia are distinct entities J Allergy Clin Immunol 2007; 120:680-7 (Year: 2007).*

(Continued)

*Primary Examiner* — Samantha L. Shterengarts
*Assistant Examiner* — Ernesto Valle, Jr.
(74) *Attorney, Agent, or Firm* — McCarter & English, LLP; Steven G. Davis; Xin Zhang

(57) ABSTRACT

The present invention relates to the use of Compound (I) or a pharmaceutically acceptable salt thereof, for the treatment of an eosinophilic disorder, including hypereosinophilic syndrome.

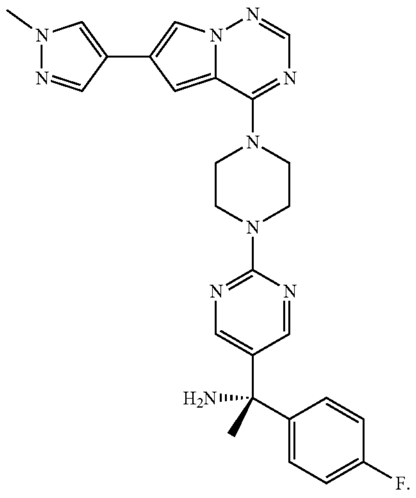

(I)

13 Claims, 4 Drawing Sheets

(56) References Cited

U.S. PATENT DOCUMENTS

| | | | |
|---|---|---|---|
| 10,807,985 B2 | 10/2020 | Hodous et al. |
| 11,046,697 B2 | 6/2021 | Wenglowsky et al. |
| 11,827,642 B2 | 11/2023 | Hodous et al. |
| 11,999,744 B2 | 6/2024 | Waetzig et al. |
| 2004/0186140 A1 | 9/2004 | Cherney et al. |
| 2006/0019280 A1 | 1/2006 | Chen et al. |
| 2006/0211695 A1 | 9/2006 | Borzilleri et al. |
| 2014/0187559 A1 | 7/2014 | Miduturu |
| 2016/0031892 A1 | 2/2016 | Hodous |
| 2016/0102097 A1 | 4/2016 | Hodous et al. |
| 2016/0311816 A1 | 10/2016 | Werner et al. |
| 2017/0022206 A1 | 1/2017 | Hodous et al. |
| 2017/0029409 A1 | 2/2017 | DiPietro et al. |
| 2017/0066773 A1 | 3/2017 | Wenglowsky et al. |
| 2017/0066812 A1 | 3/2017 | Bifulco, Jr. et al. |
| 2017/0119760 A1 | 5/2017 | Moussy et al. |
| 2017/0121312 A1 | 5/2017 | Brubaker et al. |
| 2017/0145018 A1 | 5/2017 | Wenglowsky et al. |
| 2017/0174652 A1 | 6/2017 | Bifulco, Jr. et al. |
| 2017/0204104 A1 | 7/2017 | Hodous et al. |
| 2017/0253593 A1 | 9/2017 | Bifulco, Jr. et al. |
| 2017/0267661 A1 | 9/2017 | Kim et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |
| 2018/0362613 A1 | 12/2018 | Bifulco, Jr. et al. |
| 2019/0119280 A1 | 4/2019 | Hodous et al. |
| 2020/0024280 A1 | 1/2020 | Hodous et al. |
| 2021/0147433 A1 | 5/2021 | Waetzig et al. |
| 2021/0284645 A1 | 9/2021 | Hodous et al. |
| 2022/0010382 A1 | 1/2022 | Schmidt-Kittler |
| 2022/0370465 A1 | 11/2022 | Mar et al. |
| 2023/0271971 A1 | 8/2023 | Waetzig et al. |
| 2024/0317757 A1 | 9/2024 | Hodous et al. |

FOREIGN PATENT DOCUMENTS

| | | | |
|---|---|---|---|
| CN | 103261165 A | 8/2013 |
| CN | 105658652 A | 6/2016 |
| CN | 106048023 A | 10/2016 |
| CN | 108191874 A | 6/2018 |
| CN | 109970745 A | 7/2019 |
| CN | 110003217 A | 7/2019 |
| CN | 110938077 A | 3/2020 |
| CN | 110950872 A | 4/2020 |
| CN | 112223217 A | 1/2021 |
| EP | 0200968 A1 | 11/1986 |
| JP | 2003-519698 A | 6/2003 |
| JP | 2005-503372 A | 2/2005 |
| JP | 2006-519205 A | 8/2006 |
| JP | 2007-535558 A | 12/2007 |
| JP | 2008-504366 A | 2/2008 |
| JP | 2009-514882 A | 4/2009 |
| JP | 2009-515978 A | 4/2009 |
| JP | 2009-542814 A | 12/2009 |
| JP | 2014-521624 A | 8/2014 |
| JP | 2015-520186 A | 7/2015 |
| JP | 6446040 B2 | 12/2018 |
| JP | 2019-522051 A | 8/2019 |
| RU | 2331640 C2 | 8/2008 |
| WO | WO-2000/71129 A1 | 11/2000 |
| WO | WO-2001/25220 A1 | 4/2001 |
| WO | 2001/74821 A1 | 10/2001 |
| WO | WO-2003/010158 A1 | 2/2003 |
| WO | WO-2003/090912 A1 | 11/2003 |
| WO | WO-2004/071460 A2 | 8/2004 |
| WO | WO-2004/076450 A1 | 9/2004 |
| WO | WO-2005/049032 A1 | 6/2005 |
| WO | WO-2005/117909 A2 | 12/2005 |
| WO | WO-2006/004636 A2 | 1/2006 |
| WO | WO-2006/028524 A2 | 3/2006 |
| WO | 2006/117185 A1 | 11/2006 |
| WO | WO-2007/056170 A2 | 5/2007 |
| WO | WO-2007/065100 A1 | 6/2007 |
| WO | WO-2007/085188 A1 | 8/2007 |
| WO | WO-2008/005956 A2 | 1/2008 |
| WO | WO-2009/015254 A1 | 1/2009 |
| WO | WO-2009/117157 A1 | 9/2009 |
| WO | WO-2010/002095 A2 | 1/2010 |
| WO | WO-2010/022055 A2 | 2/2010 |
| WO | WO-2010/144345 A1 | 12/2010 |
| WO | WO-2011/005119 A1 | 1/2011 |
| WO | WO-2011/103196 A1 | 8/2011 |
| WO | WO-2012/027495 A1 | 3/2012 |
| WO | 2013/059631 A1 | 4/2013 |
| WO | 2013/063000 A1 | 5/2013 |
| WO | 2014/018625 A1 | 1/2014 |
| WO | WO-2014/039714 A2 | 3/2014 |
| WO | WO-2014/100620 A2 | 6/2014 |
| WO | WO-2014/160521 A1 | 10/2014 |
| WO | WO-2015/057873 A1 | 4/2015 |
| WO | WO-2015/058129 A1 | 4/2015 |
| WO | WO-2016/022569 A1 | 2/2016 |
| WO | WO-2016/071511 A1 | 5/2016 |
| WO | WO-2017/019442 A1 | 2/2017 |
| WO | 2017/121444 A1 | 7/2017 |
| WO | WO-2018/049233 A1 | 3/2018 |
| WO | WO-2018/183712 A1 | 10/2018 |
| WO | WO-2019/034128 A1 | 2/2019 |
| WO | 2019/152719 A1 | 8/2019 |
| WO | WO-2020/102095 A1 | 5/2020 |
| WO | WO-2020/210669 A1 | 10/2020 |
| WO | WO-2021/004895 A1 | 1/2021 |
| WO | WO-2021/067917 A1 | 4/2021 |
| WO | WO-2021/079134 A1 | 4/2021 |

OTHER PUBLICATIONS

Evans,E. et al., A precision therapy against cancers driven by KIT/PDGFRA mutations Sci. Transl. Med. 9, pp. 1-11 (Year: 2017).*

Johannes Lübke et al., "Inhibitory effects of midostaurin and avapritinib on myeloid progenitors derived from patients with KIT D816V positive advanced systemic mastocytosis" Leukemia (2019) 33:1195-1205 (Year: 2019).*

Akin et al., Pioneer: A Randomized, Double-Blind, Placebo-Controlled, Phase 2 Study of Avapritinib in Patients with Indolent or Smoldering Systemic Mastocytosis with Symptoms Inadequately Controlled with Standard Therapy. American Academy of Allergy Asthma and Immunology Annual Meeting. 19 pages, Mar. 16, 2020.

Akin, Pioneer: A Randomized, Double-Blind, Placebo-Controlled, Phase 2 Study of Avapritinib in Patients with Indolent or Smoldering Systemic Mastocytosis with Symptoms Inadequately Controlled with Standard Therapy. 61st American Society of Hematology (ASH) Annual Meeting and Exposition. Poster 2950, 1 page, Dec. 7-10, 2019.

Antonescu, What lessons can be learned from the GIST paradigm that can be applied to other kinase-driven cancers. J Pathol. Jan. 2011;223(2):251-261.

Apsel Winger et al., ATP-Competitive Inhibitors Midostaurin and Avapritinib Have Distinct Resistance Profiles in Exon 17-Mutant KIT. Cancer Res. Aug. 15, 2019;79(16):4283-4292.

Bennett et al., Cecil Textbook of Medicine, 20th Edition, vol. 1, W.B. Saunders Company, Philadelphia. pp. 1004-1010, (1996).

Blueprint Medicines, 2020 Blueprint global business strategy. 32 pages, Jan. 7, 2019.

Blueprint Medicines, Blueprint Medicines Announces Part 1 Results from Pioneeer Trial Showing Broad Activity of Avapritinib Across Measures of Mast Cell Burden, Clinical Outcomes and Quality of Life in Indolent Systemic Mastocytosis. Press Release, Blueprint Medicines Corporation, 10 pages, Mar. 16, 2020.

Blueprint Medicines, Precision That Moves™ Staying one step ahead of disease. J.P. Morgan Healthcare Conference, 35 pages, Jan. 13-16, 2020.

Cairo, Crystalline Polymorphism of Organic Compounds. Topics in Current Chemistry. Design of Organic Solids. Springer. E. Weber (Ed.). vol. 198, pp. 163-208, Jan. 1998.

Cairoli et al., Prognostic impact of c-KIT mutations in core binding factor leukemias: an Italian retrospective study. Blood. May 1, 2006;107(9):3463-8.

(56) References Cited

OTHER PUBLICATIONS

Cohen, The development and therapeutic potential of protein kinase inhibitors. Curr Opin Chem Biol. Aug. 1999;3(4):459-65.
Coulson et al., The Role of KIT Mutations in Anaphylaxis. Curr Allergy Asthma Rep. Apr. 26, 2019;19(6):31.
Dermer, Another Anniversary for the War on Cancer. Bio/Technology. Mar. 1994;12:320.
Drummond et al., Preliminary Safety and Activity in a Phase 1 study of BLU-285, a Potent, Highly-Selective Inhibitor of KIT D816V in Advanced Systemic Mastocytosis (SM). American Society of Hematology Annual Meeting. 19 pages, Dec. 4, 2016.
Evans et al., A precision therapy against cancers driven by KIT/PDGFRA mutations. Sci Transl Med. Nov. 1, 2017;9(414):eaao1690, 12 pages.
Freshney, Culture of Animal Cells, a Manual of Basic Technique. Alan R. Liss, Inc. pp. 1-6, (1983).
Gilreath et al., Novel approaches to treating advanced systemic mastocytosis. Clin Pharmacol. Jul. 10, 2019;11:77-92.
Gotlib et al., Avapritinib, a Potent and Selective Inhibitor of Kit D816V, Improves Symptoms of Advanced Systemic Mastocytosis (AdvSM). American Society of Hematology Annual Meeting. 18 pages, Dec. 2, 2018.
Gotlib, Tyrosine Kinase Inhibitors in the Treatment of Eosinophilic Neoplasms and Systemic Mastocytosis. Hematol Oncol Clin North Am. Aug. 2017;31(4):643-661.
Heinrich et al., Preliminary safety and activity in a first-in-human Phase 1 study of BLU-285, a potent, highly selective inhibitor of KIT and PDGFRalpha activation loop mutants in advanced gastrointestinal stromal tumor (GIST). EORTC-NCI-AACR Molecular Targets and Cancer Therapeutics Symposium. 17 pages, Dec. 1, 2016.
Hilfiker et al., Relevance of Solid-state Properties for Pharmaceutical Products. Polymorphism: in the Pharmaceutical Industry. Wiley-VCH Verlag Gmbh & Co. Chapter 1, pp. 1-19. Feb. 6, 2006.
Huang et al., Two new KIT exon 13 mutations in one gastric gastrointestinal stromal tumor (GIST). Int J Clin Exp Pathol. Aug. 1, 2017;10(8):8863-8867.
InvivoChem—Material Safety Data Sheet (MSDS). Retrieved online at: https://www.invivochem.com/avapritinib.html. 6 pages, Apr. 21, 2017.
Kalinsky et al., A phase 2 trial of dasatinib in patients with locally advanced or stage IV mucosal, acral, or vulvovaginal melanoma: A trial of the ECOG-ACRIN Cancer Research Group (E2607). Cancer. Jul. 15, 2017;123(14):2688-2697.
Kluin-Nelemans et al., Prognostic impact of eosinophils in mastocytosis: analysis of 2350 patients collected in the ECNM Registry. Leukemia. Apr. 2020;34(4):1090-1101.
Kuang et al., Biologic Agents for the Treatment of Hypereosinophilic Syndromes. J Allergy Clin Immunol Pract. Nov.-Dec. 2017;5(6):1502-1509.
Lee et al., Correlation of imatinib resistance with the mutational status of KIT and PDGFRA genes in gastrointestinal stromal tumors: a meta-analysis. J Gastrointestin Liver Dis. Dec. 2013;22(4):413-8.
Martinelli et al., Hypereosinophilic Syndrome and Molecularly Targeted Therapy. Semin Hematol. 2007;44:S4-S16.
Paschka et al., Adverse prognostic significance of KIT mutations in adult acute myeloid leukemia with inv(16) and t(8;21): a Cancer and Leukemia Group B Study. J Clin Oncol. Aug. 20, 2006;24(24):3904-11.
Quintela et al., A Ready One-pot Preparation for Pyrrolo[2,1-f]-[1,2,4]triazine and Pyrazolo[5,1-c]pyrimido[4,5-e]-[1,2,4]triazine Derivatives. Tetrahedron. 1996;52(8):3037-3048.
Rutkowski et al., Developments in targeted therapy of advanced gastrointestinal stromal tumors. Recent Pat Anticancer Drug Discov. Jun. 2008;3(2):88-99.
Schnittger et al., KIT-D816 mutations in AML1-ETO-positive AML are associated with impaired event-free and overall survival. Blood. 2006;107:1791-1799.
Schwaab et al., KIT D816V and JAK2 V617F mutations are seen recurrently in hypereosinophilia of unknown significance. Am J Hematol. Sep. 2015;90(9):774-7.
Selleckchem, Safety Data Sheet. Retrieved online at: https://www.selleckchem.com/products/blu-285.html. 6 pages, Jan. 16, 2019.
Shallal et al., Discovery, synthesis, and investigation of the antitumor activity of novel piperazinylpyrimidine derivatives. Eur J Med Chem. Jun. 2011;46(6):2043-57.
Tamborini et al., A new mutation in the KIT ATP pocket causes acquired resistance to imatinib in a gastrointestinal stromal tumor patient. Gastroenterology. Jul. 2004;127(1):294-9.
Wu et al., Avapritinib: A Selective Inhibitor of KIT and PDGFR? that Reverses ABCB1 and ABCG2-Mediated Multidrug Resistance in Cancer Cell Lines. Mol Pharm. Jul. 1, 2019;16(7):3040-3052.
Zhang et al., Design and pharmacology of a highly specific dual FMS and KIT kinase inhibitor. Proc Natl Acad Sci U S A. Apr. 2, 2013;110(14):5689-94.
Corti et al., Differential activity of avapritinib in patients with metastases from mucosal melanoma and thymic carcinoma harbouring KIT exon 17 mutations: Initial experience from a Compassionate Use Program in Italy. Eur J Cancer. Sep. 2022;172:332-339.
Kovalszki et al., Eosinophilia in mast cell disease. Immunol Allergy Clin North Am. May 2014;34(2):357-64.
Radia, Avapritnib, A Potent and Selective Inhibitor of KIT D816 V, Induces Complete and Durable Responses in Patients (PTS) with Advanced Systemic Mastocytosis (ADVSM). HemaSphere. 2019;3(S1):368-369.
Vojvodic et al., Melanoma and Mastocytosis. Open Access Maced J Med Sci. Aug. 30, 2019;7(18):3050-3052.
Kettle et al., Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors. J Med Chem. Oct. 11, 2018;61(19):8797-8810.
Pilla Reddy et al., The Pharmacokinetic-Pharmacodynamic (PKPD) Relationships of AZD3229, a Novel and Selective Inhibitor of KIT, in a Range of Mouse Xenograft Models of GIST. Clin Cancer Res. Jul. 15, 2020;26 (14):3751-3759.
Wechsler et al., Novel targeted therapies for eosinophilic disorders. J Allergy Clin Immunol. Sep. 2012;130 (3):563-71.
International Search Report and Written Opinion for Application No. PCT/US2020/054221, dated Jan. 12, 2021, 22 pages.
Deininger et al., Avapritinib (BLU-285). a Selective KIT Inhibitor, is Associated with High Response Rate and Tolerable Safety Profile in Advanced Systemic Mastocytosis: Results of a Phase 1 Study. Retrieved online at: www.blueprintmedicines.com, 1 page, (2018).
Lubke et al., Inhibitory effects of midostaurin and avapritinib on myeloid progenitors derived from patients with KIT D816V positive advanced systemic mastocytosis. Leukemia. May 2019;33(5):1195-1205.
Pardanani, Systemic mastocytosis in adults: 2019 update on diagnosis, risk stratification and management. Am J Hematol. Mar. 2019;94(3):363-377.
Vaes et al., Targeted Treatment Options in Mastocytosis. Front Med (Lausanne). Jul. 20, 2017;4:110, 12 pages.
Bavin, Polymorphism in Process Development. Chemistry & Industry. Aug. 1989;21:527-529.
Brittain, Polymorphism in Pharmaceutical Salts, Second Edition. informa healthcare, New York. pp. 333-338, (2009).
Buttner et al., Identification of activating c-kit mutations in adult-, but not in childhood-onset indolent mastocytosis: a possible explanation for divergent clinical behavior. J Invest Dermatol. Dec. 1998;111(6):1227-31.
Byrn et al., Pharmaceutical solids: a strategic approach to regulatory considerations. Pharm Res. Jul. 1995;12 (7):945-54.
European Pharmacopoeia, Characterisation of Crystalline and Partially Crystalline Solids by X-Ray Powder Diffraction (XRPD). 2.9.33. pp. 301-305, (2011).
Evans et al., Blu-285, a Potent and Selective Inhibitor for Hematologic Malignancies with KIT Exon 17 Mutations. Blood. 2015;126(23):568, 5 pages.

(56) References Cited

OTHER PUBLICATIONS

Gotlib et al., Efficacy and Safety of Midostaurin in Advanced Systemic Mastocytosis. N Engl J Med. Jun. 30, 2016;374 (26):2530-41, with supplementary information.
Grunenberg, Polymorphie und Thermische Analyse, pharmazeutischer Wirkstoffe. Pharmazie in unserer Zeit;1997;5:224-231.
Guillory, Generation of Polymorphs, Hydrates, Solvates, and Amorphous Solids. Drugs and the Pharmaceutical Sciences. 1999;95:183-226.
Kawaguchi et al., Drug and crystal polymorphism. Journal of Human Environmental Engineering. 2002;4 (2):310-317.
Lippold et al., Lehrbuch der Pharmazeutischen Technologie. Wissenschaftliche Verlagsgesellschaft mbH Stuttgart. pp. 214-217, (2006).
Mitsuhisa, Approach to Crystal Polymorph in Process Research of New Drugs. Journal of the Society for Synthetic Organic Chemistry. 2007;65(9):907-913.
Oppelt et al., Gastrointestinal stromal tumors (GISTs): point mutations matter in management, a review. J Gastrointest Oncol. Jun. 2017;8(3):466-473.
Pharmaceutical Affairs Bureau No. 568, Establishment of Specifications and Test Methods for New Drugs. 106 pages, May 1, 2001.
Roskoski, The role of small molecule Kit protein-tyrosine kinase inhibitors in the treatment of neoplastic disorders. Pharmacol Res. Jul. 2018;133:35-52.
Schneider-Stock, BLU-285-the breakthrough in treatment of patients with aggressive systemic mastocytosis and gastrointestinal stromal tumor. Ann Transl Med. Jun. 2018;6(11):232, 2 pages.
Zamagni et al., Toward a GEP-based PET in myeloma. Blood. Jul. 6, 2017;130(1):2-3.
Declaration of Technical Expert. 6 pages, Nov. 16, 2021.
U.S. Appl. No. 14/515,327, filed Oct. 15, 2014, U.S. Pat. No. 9,200,002, Issued.
U.S. Appl. No. 14/887,614, filed Oct. 20, 2015, U.S. Pat. No. 9,994,575, Issued.
U.S. Appl. No. 15/479,145, filed Apr. 4, 2017, U.S. Pat. No. 9,944,651, Issued.
U.S. Appl. No. 15/973,378, filed May 7, 2018, U.S. Pat. No. 10,807,985, Issued.
U.S. Appl. No. 17/070,556, filed Oct. 14, 2020, 2021-0284645, Abandoned.
U.S. Appl. No. 17/983,747, filed Nov. 9, 2022, U.S. Pat. No. 11,827,642, Issued.
U.S. Appl. No. 18/382,727, filed Oct. 23, 2023, 2024-0317757, Published.
U.S. Appl. No. 17/153,727, filed Jan. 20, 2021, U.S. Pat. No. 12,60,354, Issued.
U.S. Appl. No. 18/077,431, filed Dec. 8, 2022, 2023-0124801, Allowed.
U.S. Appl. No. 18/077,466, filed Dec. 8, 2022, U.S. Pat. No. 11,964,980, Issued.
U.S. Appl. No. 18/543,793, filed Dec. 18, 2023, U.S. Pat. No. 11,999,744, Issued.
U.S. Appl. No. 18/800,215, filed Aug. 12, 2024, Pending.
U.S. Appl. No. 17/292,965, filed May 11, 2021, 2022-0010382, Published.
U.S. Appl. No. 17/773,447, filed Apr. 29, 2022, 2022-0370465, Abandoned.
Deangelo et al., Clinical Activity in a Phase 1 Study of Blu-285, a Potent, Highly-Selective Inhibitor of KIT D816V in Advanced Systemic Mastocytosis. Blood. Dec. 8, 2017;130(1):5 pages.
Gotlib, Phase I Study of Avapritinib in Advanced Systemic Mastocytosis. Stanford Cancer Center, slideshow, 23 pages, Oct. 2019.
Gotlib, Tyrosine Kinase Inhibitors and Therapeutic Antibodies in Advanced Eosinophilic Disorders and Systemic Mastocytosis. Curr Hematol Malig Rep. Dec. 2015;10(4):351-61.

* cited by examiner

TREATMENT OF EOSINOPHILIC DISORDERS WITH AVAPRITINIB

CROSS-REFERENCE TO RELATED APPLICATIONS

This application is a 35 U.S.C. § 371 national stage filing of International Application No. PCT/US2020/054221, filed on Oct. 5, 2020, which claims priority from U.S. Provisional Application No. 62/910,931, filed on Oct. 2, 2019. The entire contents of each of the aforementioned applications are incorporated herein by reference.

BACKGROUND

Eosinophils are bone marrow-derived granulocytes implicated beneficially in host defense against infection, in antitumor cytotoxicity, and in wound healing. Eosinophils are implicated in various diseases including allergic diseases and are thought to play an important role in generating morbidity of allergic diseases, such as chronic bronchial asthma and atopic dermatitis (Adv. Immunol., 39, 177 (1986), Immunol. Today, 13, 501 (1992)). In addition to the above diseases, eosinophils are also implicated in diseases generally referred to as hypereosinophilic syndrome (HES), eosinophilia, eosinophilic enterogastritis, eosinophilic leukemia, eosinophilic granuloma and Kimura's disease (Ann. Intern. Med., 97, 78 (1982)).

Eosinophils are divided into subgroups, normodense eosinophils and hypodense eosinophils. Eosinophils have been shown to be hypodense eosinophils upon activation (Immunology, 47, 531 (1982)). Hypodense eosinophils are also referred to as activated eosinophils. It has been reported that a qualitative change occurs in addition to a quantitative change in eosinophils in the peripheral blood of an HES patients (Clin. Exp. Immunol., 24, 423 (1976)). Activated eosinophils have been implicated in the severity of HES symptom (Am. J. Cardiol., 52, 321 (1983)). Aside from HES patients, activated eosinophils have been also found in the peripheral blood, and in bronchoalveolar lavage fluid (BALE) of patients with bronchial asthma (Am. Rev. Respir. Dis, 132, 981 (1985)). Various receptors, such as those of cytokines, are expressed on activated eosinophils (hypodense eosinophils) (J. Immunol., 142, 4416 (1989)). Compared to normodense eosinophils, these hypodense eosinophils show elevated sensitivities against IL-5 (Clin. Exp. Immunol., 85, 312 (1991); J. Exp. Med., 172, 1347 (1990)).

Currently, treatment for patients with eosinophilic diseases consists of administration of steroids. However, steroid administration is often associated with side effects. Specifically, the treatment has some other problems, such that patient's pathological condition may return to the original state when steroid administration is discontinued, and prolonged steroid administration may induce steroid resistance. Accordingly, there is a need for safe and effective treatments for eosinophil related disorders.

SUMMARY

It now has been found that Compound (I) as shown below effectively reduces eosinophil levels (Example 1) in patients. Based on this discovery, methods of reducing eosinophil levels in a subject in need thereof with Compound (I) or a pharmaceutically acceptable thereof are disclosed herein.

(I)

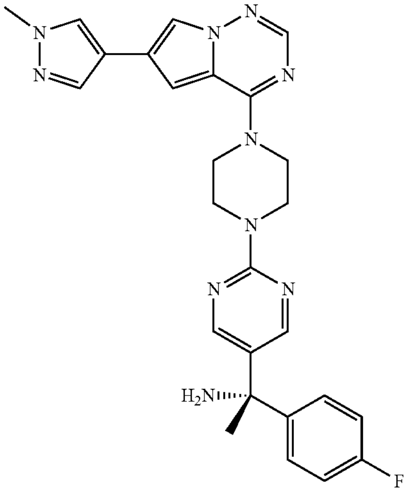

One aspect of the present disclosure is a method of treating an eosinophilic disorder, comprising administering to a subject in need thereof a therapeutically effective amount of Compound (I) or a pharmaceutically acceptable salt thereof.

Another aspect of the present disclosure is the use of Compound (I) or a pharmaceutically acceptable salt thereof for the manufacture of a medicament for treating an eosinophilic disorder.

Another aspect of the present disclosure is Compound (I) or a pharmaceutically acceptable salt thereof for treating an eosinophilic disorder.

DETAILED DESCRIPTION

Figure 1:
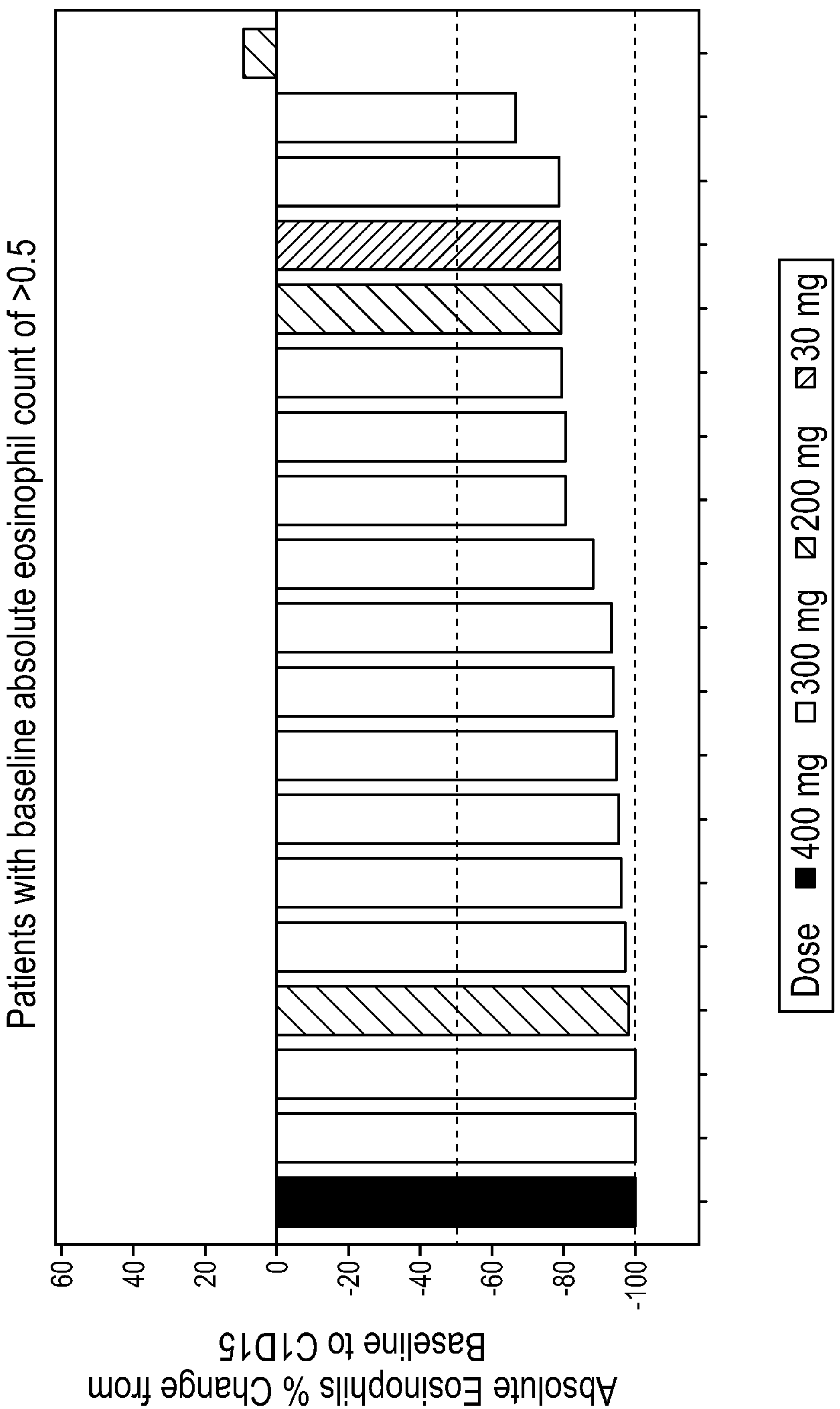
FIG. 1 shows the absolute eosinophil changes from baseline levels for C1D15 (cycle 1 day 15) in adult patients treated with Compound (I) in a Phase 1 clinical trial after 2 weeks. The dose range of Compound (I) is between 30 mg and 400 mg. The patients with baseline absolute eosinophil count of >0.5.

Eosinophils have been implicated in the pathogenesis of numerous diseases and disorders. Eosinophils are a type of white blood cell, which help fight off infections and play a role in body's immune response. They are a normal cellular component of the blood and also of certain tissues, including spleen, lymph nodes, thymus, and the submucosal areas of the gastrointestinal, respiratory, and genitourinary tracts. Counts of 0 to 450 eosinophils per cubic millimeter of blood are considered within normal limits.

Eosinophilic disorders occur when eosinophils are found in above-normal amounts in various parts of the body and/or when there is a higher than normal ratio of hypodense versus normodense esosinophils (e.g., greater than 30%). The eosinophilic disorder described herein are characterized by an overabundance of eosinophils (eosinophilia). The increased number of eosinophils inflame tissues and cause organ damage. The heart, lungs, skin, and nervous system are most often affected, but any organ can be damaged.

Eosinophilic disorders are diagnosed according to the location where the levels of eosinophils are elevated:

- Eosinophilic pneumonia (lungs)
- Eosinophilic cardiomyopathy (heart)
- Eosinophilic esophagitis (esophagus—EoE)
- Eosinophilic gastritis (stomach—EG)
- Eosinophilic gastroenteritis (stomach and small intestine—EGE)
- Eosinophilic enteritis (small intestine)
- Eosinophilic colitis (large intestine—EC)
- Hypereosinophilic syndrome (blood and any organ—HES)

Additionally, non-limiting examples of diseases and disorders in which eosinophils play a role (i.e., eosinophilic disorders) are: asthma, immunoglobulin (IgE)-mediated food allergy, eosinophilic esophagitis (inflammation of the esophagus), inflammatory bowel disease, COPD, allergic colitis, astro-esophageal reflux, eosinophilic gastrointestinal disease (EGID), eosinophilic gastroenteritis, endomyocardial fibrosis, Loeffler's endocarditis. Davies disease, episodic angioedema associated with eosinophilia, eosinophilia-myalgia syndrome/Spanish toxic oil syndrome, liver cirrhosis, dermatitis herpetiformis, Bullous pemphigoid, Churg-Strauss syndrome, acute myelogenous eosinophilic leukemia, acute lymphocytic eosinophilic leukemia, systemic mastocytosis with eosinophilia, allergic rhinitis, eczema, Wegener's granulomatosis, polyarteritis nodosa, eosinophilic fasciitis, and rheumatoid arthritis.

Accordingly, one aspect of the present disclosure is a method of treating an eosinophilic disorder, comprising administering to the subject a therapeutically effective amount of Compound (I) or a pharmaceutically acceptable salt thereof. In one embodiment, the eosinophilic disorder is selected from hypereosinophilic syndrome, eosinophilia, eosinophilic enterogastritis, eosinophilic leukemia, eosinophilic granuloma and Kimura's disease.

In one embodiment, the eosinophilic disorder is hypereosinophilic syndrome. In a specific embodiment, the hypereosinophilic syndrome is idiopathic hypereosinophilic syndrome. In one embodiment, the eosinophilic disorder is eosinophilic leukemia. In a specific embodiment, the eosinophilic leukemia is chronic eosinophilic leukemia. In another embodiment, the eosinophilic disorder is refractory to treatment with imatinib, sunitinib, and/or regorafenib. In a specific embodiment, the eosinophilic disorder is refractory to treatment with imatinib.

Another aspect of the present disclosure is a method of reducing the number of eosinophils in a subject in need thereof comprising administering to the subject a therapeutically effective amount of Compound (I) or a pharmaceutically acceptable salt thereof.

In one embodiment, the disclosed methods reduce the number of eosinophils in the blood, bone marrow, gastrointestinal tract (e.g., esophagus, stomach, small intestine and colon), or lung. In another embodiment, a method disclosed herein reduces the number of blood eosinophils. In a further embodiment, a method disclosed herein reduces the number of lung eosinophils. In still a further embodiment, a method disclosed herein reduces the number of eosinophil precursor cells.

In another embodiment, the disclosed methods reduce (post-administration) the number of eosinophils by at least about 10%, at least about 20%, at least about 30%, at least about 40%, at least about 50%, at least about 60%, at least about 70%, at least about 80%, at least about 90%, at least about 95% or at least about 99%. In a specific embodiment, a method disclosed herein reduces the number of eosinophils below the limit of detection.

In another embodiment, the disclosed methods reduce (post-administration) the number of eosinophil precursors by at least about 10%, at least about 20%, at least about 30%, at least about 40%, at least about 50%, at least about 60%, at least about 70%, at least about 80%, at least about 90%, at least about 95% or at least about 99%. In a specific embodiment, a method disclosed herein reduces the number of eosinophil precursors below the limit of detection.

In a further embodiment, the disclosed methods reduce eosinophils to a level below detection following a single administration of Compound (I) or a pharmaceutically acceptable salt thereof. In a specific embodiment, a single administration of Compound (I) or a pharmaceutically acceptable salt thereof reduces eosinophils to a level below detection for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

In a further embodiment, the disclosed methods reduce eosinophil precursors following a single administration of Compound (I) or a pharmaceutically acceptable salt thereof. In a specific embodiment, a single administration of Compound (I) or a pharmaceutically acceptable salt thereof reduces eosinophil precursors to a level below detection for at least about 1 day, at least about 2 days, at least about 3 days, at least about 4 days, at least about 5 days, at least about 6 days, at least about 7 days, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 12 weeks, at least about 14 weeks, at least about 16 weeks, at least about 20 weeks, or at least about 25 weeks.

The disclosure provides a method of treating an eosinophilic disorder, comprising administering to a subject in need thereof an amount of 30 mg to 400 mg (e.g., 100 mg to 300 mg, or 200 mg to 300 mg) of Compound (I) and/or a pharmaceutically acceptable salt thereof once a day. In some embodiments, the amount is 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg once a day. In some embodiments, the amount is 25 mg once a day. In some embodiments, the amount is 50 mg once a day. In some embodiments, the amount is 75 mg once a day. In some embodiments, the amount is 100 mg once a day. In some embodiments, the amount is 150 mg once a day. In some embodiments, the amount is 200 mg once a day. In some embodiments, the amount is 250 mg once a day. In some embodiments, the amount is 300 mg once a day.

As used herein, "Compound (I)" refers to a compound having a chemical name (S)-1-(4-fluorophenyl)-1-(2-(4-(6-(1-methyl-1H-pyrazol-4-yl)pyrrolo[2,1-f][1,2,4]triazin-4-yl)piperazin-yl)pyrimidin-5-yl)ethan-1-amine, which has the following structure:

(I)

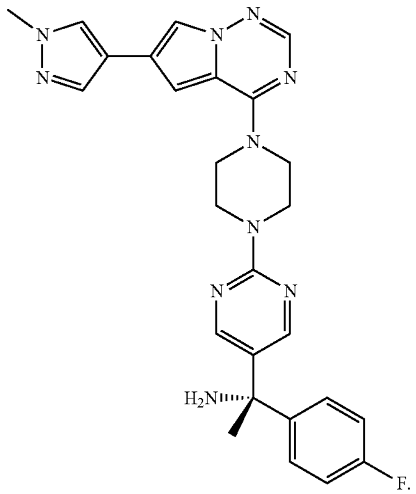

Compound (I) is disclosed in WO 2015/057873, the entire teachings of which are incorporated herein by reference. The preparation of Compound (I) is described in Example 7 of WO 2015/057873.

Compound (I) was developed to selectively target KIT D816V and other KIT exon 17 mutations, and has demonstrated potent and selective activity against KIT D816V in vitro, robust growth inhibition in a tyrosine kinase inhibitor (TKI)-resistant mastocytoma model in vivo, and tolerability at active doses in toxicology and safety pharmacology studies. An ongoing Phase 1 study of Compound (I) in patients with advanced systemic mastocytosis (AdvSM) (NCT02561988) is evaluating safety and preliminary efficacy. The recommended Phase 2 dose (RP2D) was identified as 300 mg once a day (QD), and an expansion cohort of the study is further evaluating efficacy and safety of this dose in a larger cohort of patients, as well as validating the AdvSM Symptom Assessment Form (AdvSM-SAF) that has been developed to assess the impact of Compound (I) on symptom improvement in patients with AdvSM. Based on emerging safety and efficacy data in patients treated at 300 mg QD, an additional cohort of patients treated at 200 mg QD was added.

Activating mutations at the D816 position are found in eosinophilic disorders, with the most common mutations being D816V and D816Y. The D816V mutation is found in the activation loop of the kinase domain and leads to constitutive activation of KIT kinase.

Primary treatment with a KIT inhibitor such as imatinib has also been shown to be beneficial for initial treatment of eosinophilic disorders. Specifically, imatinib is approved for the treatment of idocratic hypereosinophilic syndrome. However, resistance to imatinib occurs within months through somatic mutation. These secondary imatinib resistant mutations are most frequently located on Exon 11, 13, 14, 17 or 18. There is a need for therapeutic agents to treat patients with eosinophilic disorders, specifically patients who have exon 17 mutations.

Compound (I) or a pharmaceutically acceptable salt thereof can be active against one or more KIT mutations in Exon 17 (e.g., D816V, D816Y, D816F, D816K, D816H, D816A, D816G, D820A, D820E, D820G, N822K, N822H, Y823D, and A829P), and much less active against wild-type KIT.

In one embodiment, Compound (I) or a pharmaceutically acceptable salt thereof can be active against a D816 mutation in KIT in Exon 17. In a specific embodiment, the D816 mutation is D816V. In another specific embodiment, the D816 mutation is D816Y.

As used herein, the term "pharmaceutically acceptable salt" refers to a non-toxic salt form of a compound of this disclosure. Pharmaceutically acceptable salts of Compound (I) include those derived from suitable inorganic and organic acids and bases. Pharmaceutically acceptable salts are well known in the art. Suitable pharmaceutically acceptable salts are, e.g., those disclosed in Berge, S. M., et al. *J. Pharma. Sci.* 66:1-19 (1977). Non-limiting examples of pharmaceutically acceptable salts disclosed in that article include: acetate; benzenesulfonate; benzoate; bicarbonate; bitartrate; bromide; calcium edetate; camsylate; carbonate; chloride; citrate; dihydrochloride; edetate; edisylate; estolate; esylate; fumarate; gluceptate; gluconate; glutamate; glycollylarsanilate; hexylresorcinate; hydrabamine; hydrobromide; hydrochloride; hydroxynaphthoate; iodide; isethionate; lactate; lactobionate; malate; maleate; mandelate; mesylate; methylbromide; methylnitrate; methylsulfate; mucate; napsylate; nitrate; pamoate (embonate); pantothenate; phosphate/diphosphate; polygalacturonate; salicylate; stearate; subacetate; succinate; sulfate; tannate; tartrate; teociate; triethiodide; benzathine; chloroprocaine; choline; diethanolamine; ethylenediamine; meglumine; procaine; aluminum; calcium; lithium; magnesium; potassium; sodium; and zinc.

Non-limiting examples of pharmaceutically acceptable salts derived from appropriate acids include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid, or malonic acid; and salts formed by using other methods used in the art, such as ion exchange. Additional non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Non-limiting examples of pharmaceutically acceptable salts derived from appropriate bases include alkali metal, alkaline earth metal, ammonium, and N+(C1-4 alkyl)4 salts. This disclosure also envisions the quaternization of any basic nitrogen-containing groups of the compounds disclosed herein. Non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate, and aryl sulfonate. Other non-limiting examples of pharmaceutically acceptable salts include besylate and glucosamine salts.

As used herein, "a therapeutically effective amount" of a compound disclosed herein refers to an amount of the compound that will elicit a biological or medical response in a subject, e.g., reduce or inhibit enzyme or protein activity, ameliorate symptoms, alleviate conditions, or slow or delay disease progression.

As used herein, the term "patient" or "subject" refers to an organism to be treated by the methods of the disclosure. Non-limiting example organisms include mammals, e.g., murines, simians, equines, bovines, porcines, canines, felines, and the like. In some embodiments, the organism is a human.

As used herein, the term "treat," "treating," or "treatment," when used in connection with a disorder or condition, includes any effect, e.g., lessening, reducing, modulating, ameliorating, and/or eliminating, that results in the improvement of the disorder or condition. Improvements in or lessening the severity of any symptom of the disorder or condition can be readily assessed according to standard methods and techniques known in the art.

Hypereosinophilic syndrome is a group of blood disorders that are characterized by high numbers of eosinophils—white blood cells that play an important role in immune system. Over time, the excess eosinophils enter various tissues, eventually damaging organs.

The contemporary classification of HES includes (1) idiopathic HES in which the cause of HE remains unknown, (2) primary (neoplastic) HES in which eosinophils are found to be clonal, and (3) secondary (reactive) HES with the presence of cytokine-driven non-clonal HE. A unique form of secondary HES is called lymphocytic in which aberrant T-cells can be identified in blood.

Pharmaceutical Compositions

Compound (I) and/or pharmaceutically acceptable salts thereof described herein are useful as an active pharmaceutical ingredients (API) as well as materials for preparing pharmaceutical compositions that incorporate one or more pharmaceutically acceptable excipients and is suitable for administration to human subjects.

In some embodiments, the disclosure provides a pharmaceutical composition comprising Compound (I) and/or a pharmaceutically acceptable salt thereof and at least one additional pharmaceutically acceptable excipient. The term "pharmaceutically acceptable excipient," as used herein, refers to a pharmaceutically acceptable material, composition, and/or vehicle, such as a liquid or solid filler, diluent, excipient, solvent, or encapsulating material. Each excipient must be "pharmaceutically acceptable" in the sense of being compatible with the subject composition and its components and not injurious to the patient. Except insofar as any conventional pharmaceutically acceptable excipient is incompatible with Compound (I) and/or pharmaceutically acceptable salts thereof, such as by producing any undesirable biological effect or otherwise interacting in a deleterious manner with any other component(s) of the pharmaceutically acceptable composition, its use is contemplated to be within the scope of this disclosure.

Some non-limiting examples of materials which may serve as pharmaceutically acceptable excipients include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Remington: The Science and Practice of Pharmacy, 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, also disclose additional non-limiting examples of pharmaceutically acceptable excipients, as well as known techniques for preparing and using the same.

Pharmaceutical compositions disclosed herein may be administered orally, parenterally, by inhalation spray, topically, rectally, nasally, buccally, vaginally, or via an implanted reservoir. The term "parenteral," as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the pharmaceutical compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Non-limiting examples of acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

Pharmaceutical compositions disclosed herein may also be orally administered in any orally acceptable dosage form including, but not limited to, capsules, tablets, aqueous suspensions, or solutions. When aqueous suspensions are required for oral use, the active ingredient is typically combined with emulsifying and suspending agents. If desired, certain sweetening, flavoring, or coloring agents may also be added. In some embodiments, the pharmaceutical composition comprising Compound (I) and/or a pharmaceutically acceptable salt thereof is a tablet prepared using methods known in the art. In some embodiments, the tablet is an immediate release tablet for oral administration. In some embodiments, Compound (I) and/or a pharmaceutically acceptable salt thereof is blended with pharmacopeial excipients to form an immediate release tablet. In some embodiments, the excipients comprising the tablet are microcrystalline cellulose, copovidone, croscarmellose sodium, and magnesium sterate. In some embodiments, the formulation blend is roller compacted, compressed into round tablets, and aesthetically film coated.

EXEMPLIFICATION

The following examples are intended to be illustrative and are not intended to be limiting in any way to the scope of the disclosure.

Example 1

This is a Phase 1, open-label, study designed to evaluate the safety, tolerability, PK, PD, and preliminary antineoplastic activity of Compound (I), administered orally, in adult patients with advanced systemic mastocytosis (AdvSM) and relapsed or refractory myeloid malignancies.

The study consists of 2 parts: dose-escalation (Part 1) and expansion (Part 2). Approximately 25 patients were in Part 1 and approximately 55 patients were in Part 2.

Systemic mastocytosis diagnosis confirmation for study eligibility is to be assessed using the WHO criteria for diagnosis and subclassification. Evaluable C-findings per modified IWG-MRT-ECNM criteria are to be used to assess response.

A treatment cycle is 28 days in duration. Patients presented to the study center on C1D1 for the first dose of study drug and serial PK sampling, PD sample collection, vital sign measurement, electrocardiogram (ECG) monitoring, patient general impression of symptom severity (PGIS) and European Organization for Research and Treatment of Cancer Core Quality of Life Questionnaire (EORTC QLQ-C30), safety monitoring and adverse event (AE) recording.

Advanced SM response were assessed by imaging (magnetic resonance imaging [MRI] or computed tomography [CT]) and bone marrow (BM) evaluation at C3D1, C5D1 (imaging only), C7D1, C11D1, and C18D1. After C18, AdvSM response were assessed every 6 cycles.

All patients attended an end of treatment (EOT) visit within 14 (±7) days after the last dose of study drug. The EOT visit must occur no more than 21 days after last dose of study drug.

Part 1 (Dose Escalation)

Patients with AdvSM or a relapsed or refractory myeloid malignancy were enrolled in the dose escalation part of the study. A 3+3 dose-escalation design using cohorts of 3 patients were employed.

The first cohort of patients received Compound (I) at a starting dose of 30 mg once daily (QD). Dose escalation proceeded at increments up to 100% until ≥1 patient treated at a given dose level has a ≥Grade 2 non-hematologic AE or a Grade 4 hematologic AE and the AE (non-hematologic or hematologic) was not clearly attributable to a cause other than Compound (I) or the dose exceeds the highest dose determined to be safe in the ongoing Compound (I) first-in-human (FIH) study in GIST, BLU-285-1101.

Three patients were enrolled initially in each cohort and an additional 3 patients (for a total of 6) were enrolled when the cohort requires expansion due to dose-limiting toxicity (DLT). Dose escalation continued until the maximum tolerated dose (MTD) or a recommended phase 2 dose (RP2D) below the MTD were determined.

Part 2 (Expansion)

Once the MTD or RP2D were determined, up to 3 groups of patients with the following diagnoses of AdvSM were enrolled in Part 2 and treated with Compound (I) at the RP2D.

Patients with ASM.

Patients with SM-AHN.

Patients with MCL.

Based on available efficacy, PK, and long-term safety data, Compound (I) 200 mg QD were selected as the starting dose for the remainder of the study; all patients newly enrolled into Part 2 of the study received 200 mg as their starting dose.

Part 2 enrolled 2 cohorts. Patients who do not have measurable C-findings per modified IWG-MRT-ECNM criteria at Baseline, attributed to SM, were enrolled in cohort 1. Patients who have at least 1 measurable C-finding per modified IWG-MRT-ECNM criteria at Baseline, attributed to SM, were enrolled in cohort 2. The patients in Cohort 2 was the evaluable population for the primary objective of determining ORR, based on modified IWG-MRT-ECNM as adjudicated by the Response Adjudication Committee (RAC).

Measurement of Eosinophils

Eosinophils in patients were measured at C1D15 (cycle 1, day 15) via a routine blood test, see, e.g., LaGow B et al., eds. PDR Lab Advisor. A Comprehensive Point-of-Care Guide for Over 600 Lab Tests. 1st ed. Montvale, NJ: Thomson PDR, 2007; Pagana K, Pagana T J eds. Mosby's Manual of Diagnostic and Laboratory Tests. 5th Ed. St. Louis, Missouri. 2014; https://www.ebmconsult.com/articles/lab-test-eosinophil-count and https://www.cancer.net/cancer-types/leukemia-eosinophilic/diagnosis.

The entire teachings of the above-mentioned references and webpages are incorporated herein by reference.

Figure 2:
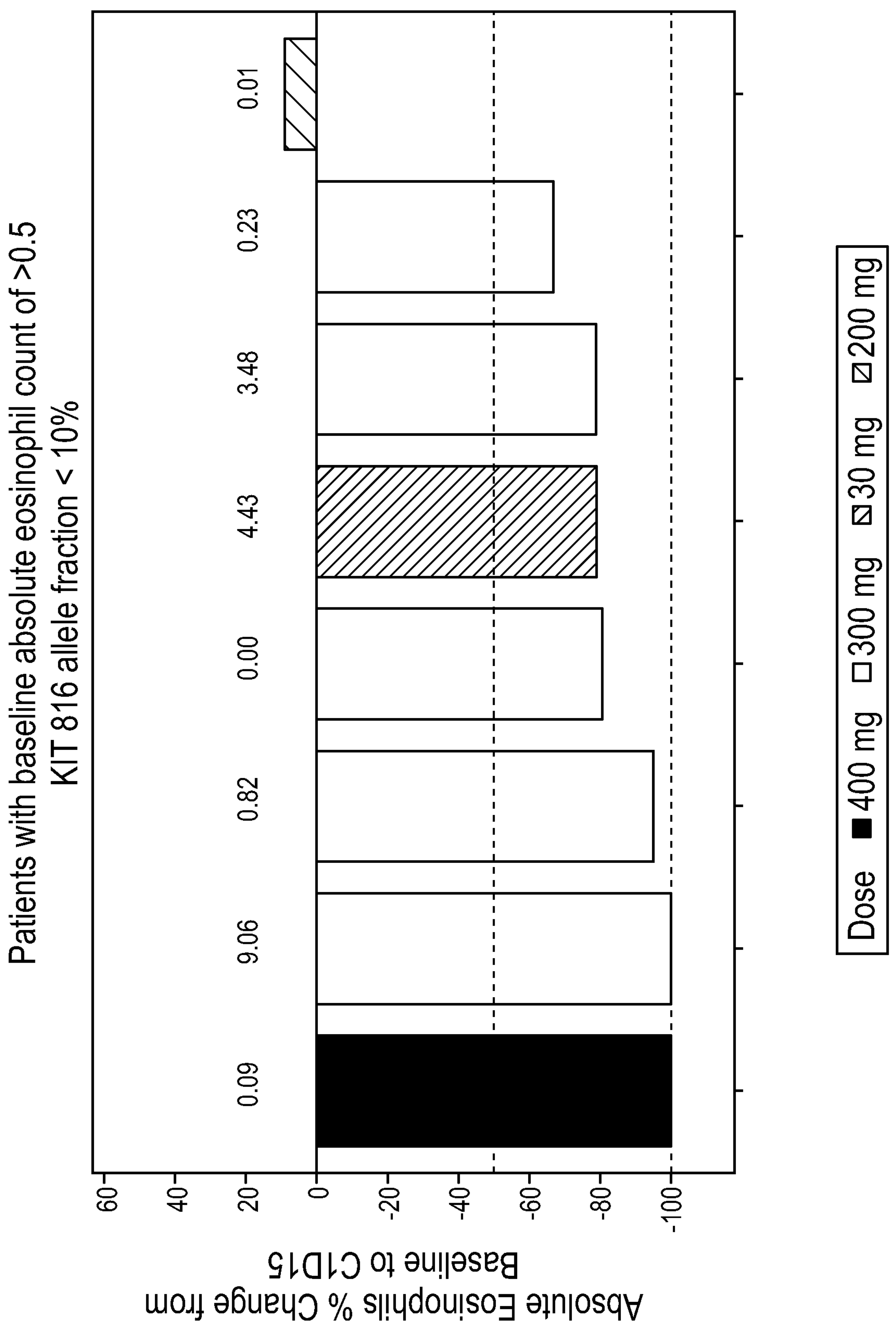
FIG. 2 shows the absolute eosinophil changes from baseline levels for C1D15 (cycle 1 day 15) in adult patients with KIT allele fraction <10% treated with Compound (I) in a Phase 1 clinical trial after 2 weeks. The dose range of Compound (I) is between 30 mg and 400 mg. The patients with baseline absolute eosinophil count of >0.5.
Figure 3:
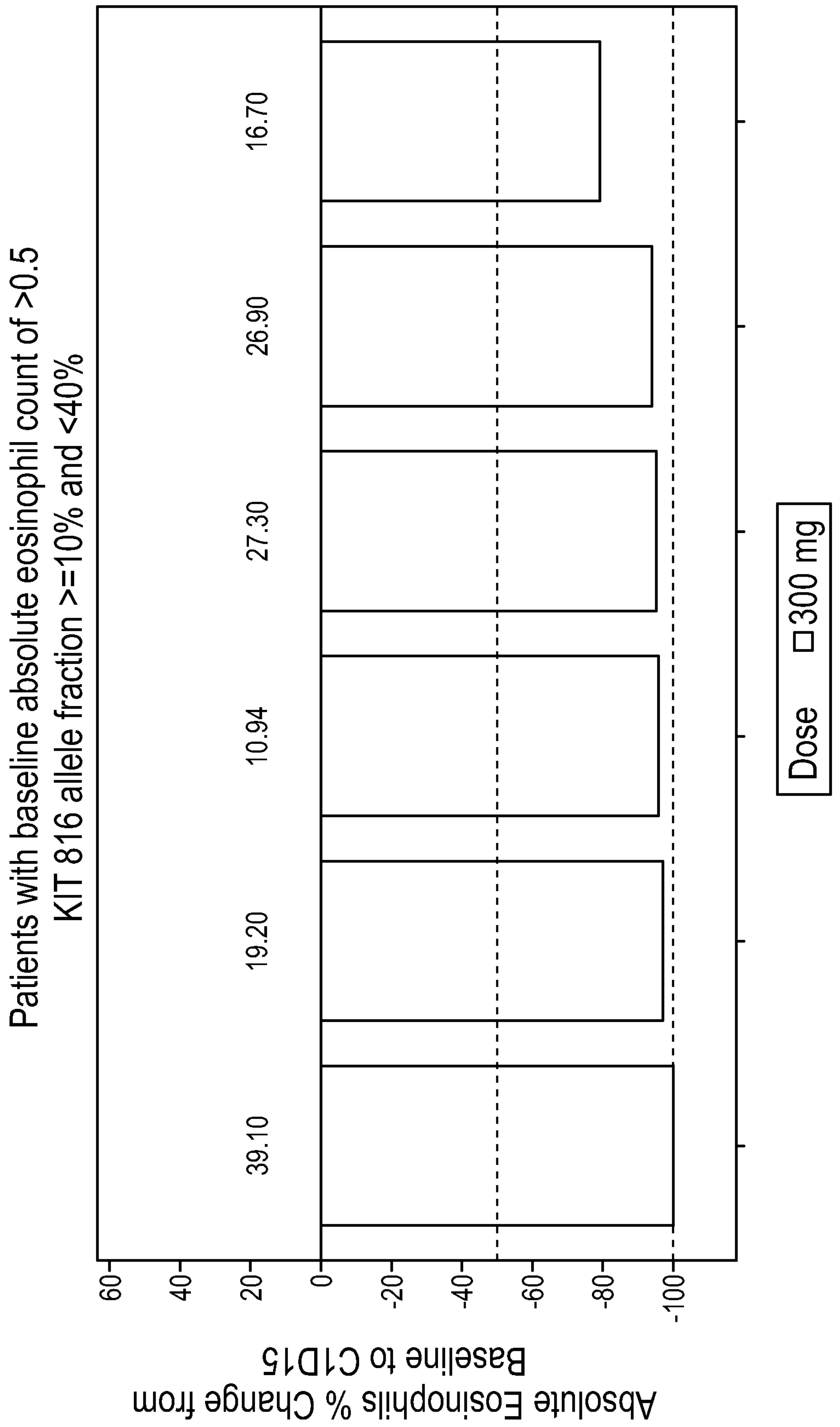
FIG. 3 shows the absolute eosinophil changes from baseline levels for C1D15 (cycle 1 day 15) in adult patients with KIT allele fraction between 10% and 40% treated with Compound (I) (with a dose of 300 mg) in a Phase 1 clinical trial after 2 weeks. The patients with baseline absolute eosinophil count of >0.5.
Figure 4:
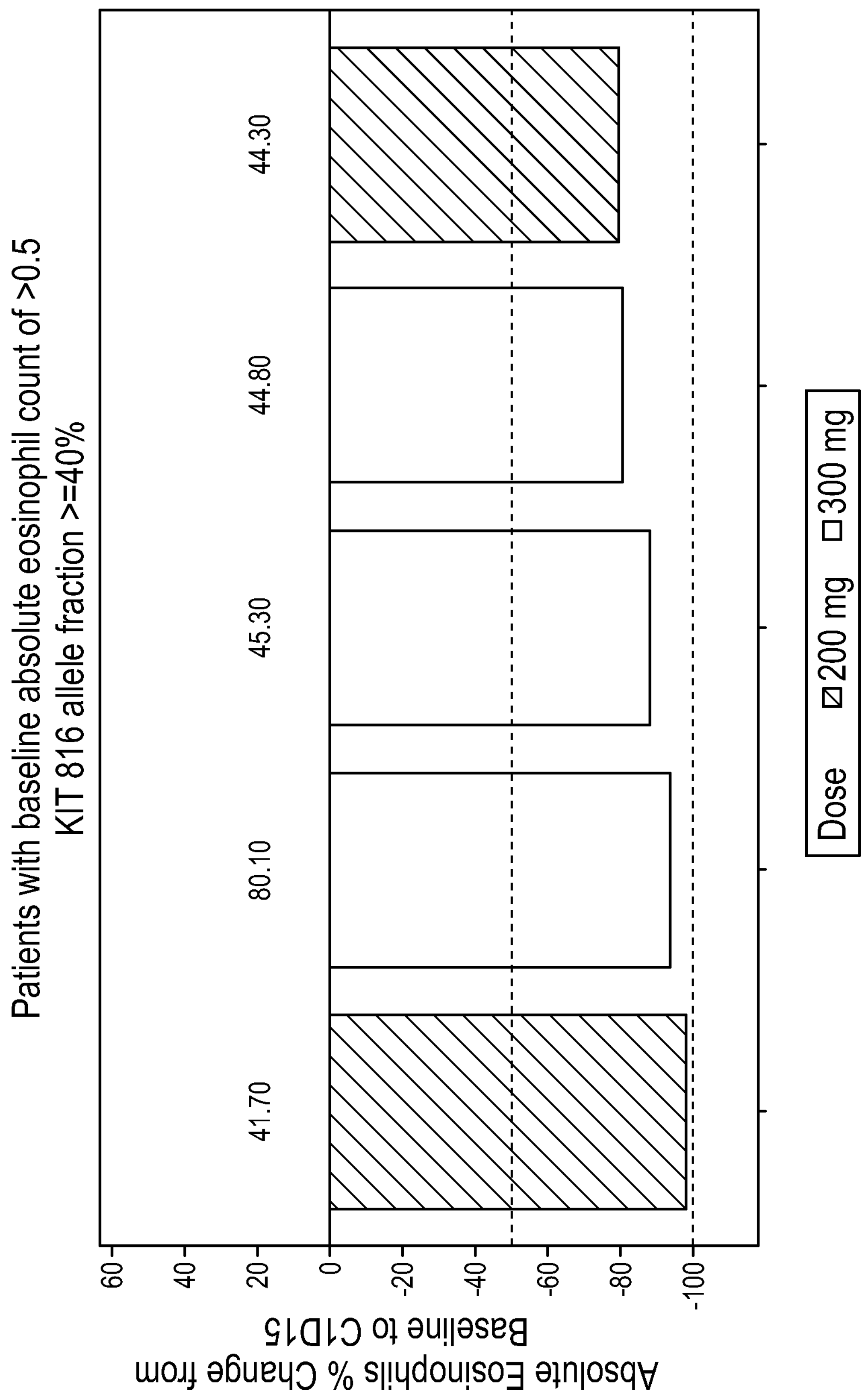
FIG. 4 shows the absolute eosinophil changes from baseline levels for C1D15 (cycle 1 day 15) in adult patients with KIT allele fraction >40% treated with Compound (I) in a Phase 1 clinical trial after 2 weeks. The dose range of Compound (I) is between 200 mg and 300 mg. The patients with baseline absolute eosinophil count of >0.5.

The test results are demonstrated in FIGS. 1-4, which show that administration of Compound (I) significantly decreases number of absolute eosinophils in patients.

The invention claimed is:

1. A method of treating an eosinophilic disorder, comprising administering to a subject in need thereof a therapeutically effective amount of Compound (I):

(I)

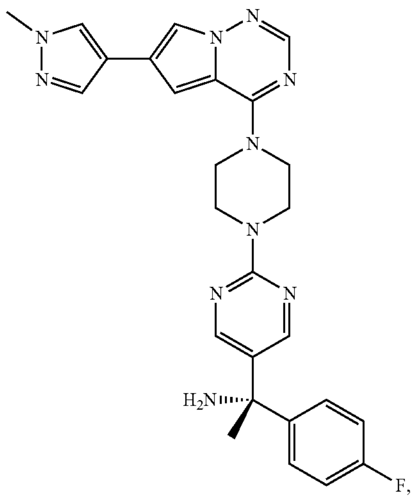

or a pharmaceutically acceptable salt thereof, wherein the eosinophilic disorder is selected from hypereosinophilic syndrome, eosinophilia, eosinophilic enterogastritis, eosinophilic granuloma and Kimura's disease.

2. The method of claim 1, wherein the eosinophilic disorder is refractory to treatment with imatinib, sunitinib, or regorafenib.

3. The method of claim 1, wherein the subject has a mutation in Exon 17 in KIT.

4. The method of claim 1, wherein the subject has a D816 mutation in KIT in Exon 17.

5. The method of claim 4, wherein the D816 mutation is D816V.

6. The method of claim 4, wherein the D816 mutation is D816Y.

7. The method of claim 1, wherein the therapeutically effective amount is 30-400 mg.

8. The method of claim 1, wherein the therapeutically effective amount is 100-300 mg per day.

9. The method of claim 1, wherein the therapeutically effective amount is 100 mg per day.

10. The method of claim 1, wherein the therapeutically effective amount is 200 mg per day.

11. The method of claim 1, wherein the therapeutically effective amount is 300 mg per day.

12. The method of claim 1, wherein the eosinophilic disorder is selected from eosinophilic enterogastritis, eosinophilic granuloma and Kimura's disease.

13. The method of claim 1, wherein the eosinophilic disorder is refractory to treatment with imatinib, sunitinib, and regorafenib.

* * * * *